(12) United States Patent
Dillon et al.

(10) Patent No.: US 9,592,142 B2
(45) Date of Patent: Mar. 14, 2017

(54) INNER CATHETER ARRANGEMENT FOR A SELF-EXPANDING MEDICAL DEVICE DELIVERY SYSTEM

(71) Applicant: Cook Medical Technologies LLC, Bloomington, IN (US)

(72) Inventors: Conor M. Dillon, Tipperary (IE); John Neilan, Galway (IE); Brent A. Mayle, Spencer, IN (US); James C. Merk, Terre Haute, IN (US); Dean R. Puckett, Bloomington, IN (US); Tiffani L. Cannon, Bloomington, IN (US); Darin Voorhies, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 217 days.

(21) Appl. No.: 14/180,064

(22) Filed: Feb. 13, 2014

(65) Prior Publication Data

US 2014/0236279 A1    Aug. 21, 2014

Related U.S. Application Data

(60) Provisional application No. 61/765,252, filed on Feb. 15, 2013.

(51) Int. Cl.
*A61F 2/966* (2013.01)

(52) U.S. Cl.
CPC ......... *A61F 2/966* (2013.01); *Y10T 29/49874* (2015.01)

(58) Field of Classification Search
CPC .. A61F 2/95; A61F 2/962; A61F 2/966; A61F 2002/9517; A61F 2002/9522; A61F 2002/9665

See application file for complete search history.

(56) References Cited

U.S. PATENT DOCUMENTS

| 4,382,445 | A | | 5/1983 | Sommers | |
|---|---|---|---|---|---|
| 5,460,608 | A | | 10/1995 | Lodin et al. | |
| 5,662,622 | A | | 9/1997 | Gore et al. | |
| 6,042,589 | A | | 3/2000 | Marianne | |
| 6,159,228 | A | * | 12/2000 | Frid | A61F 2/95 606/108 |
| 7,527,632 | B2 | | 5/2009 | Houghton et al. | |
| 7,625,337 | B2 | | 12/2009 | Campbell et al. | |
| 7,887,529 | B2 | | 2/2011 | Eder | |
| 7,955,970 | B2 | | 6/2011 | Sunayama et al. | |
| 2007/0060996 | A1 | * | 3/2007 | Goodin | A61F 2/95 623/1.11 |
| 2007/0191925 | A1 | | 8/2007 | Dorn | |
| 2009/0074477 | A1 | | 3/2009 | Mori et al. | |
| 2010/0036363 | A1 | | 2/2010 | Watanabe et al. | |
| 2010/0057051 | A1 | | 3/2010 | Howat et al. | |

FOREIGN PATENT DOCUMENTS

EP    0 747 022 A2    12/1996

\* cited by examiner

*Primary Examiner* — Ryan J Severson
*Assistant Examiner* — Christian Knauss
(74) *Attorney, Agent, or Firm* — Brinks Gilson & Lione

(57) ABSTRACT

A delivery system for a self-expanding medical device is provided. The delivery system includes an outer sheath that radially restrains the medical device. First and second inner catheters are disposed within the outer sheath. The first inner catheter is a composite structure with a closed coil wire covered by a polymer outer layer. The second inner catheter is disposed within the closed coil wire but is not attached to the closed coil wire.

18 Claims, 1 Drawing Sheet

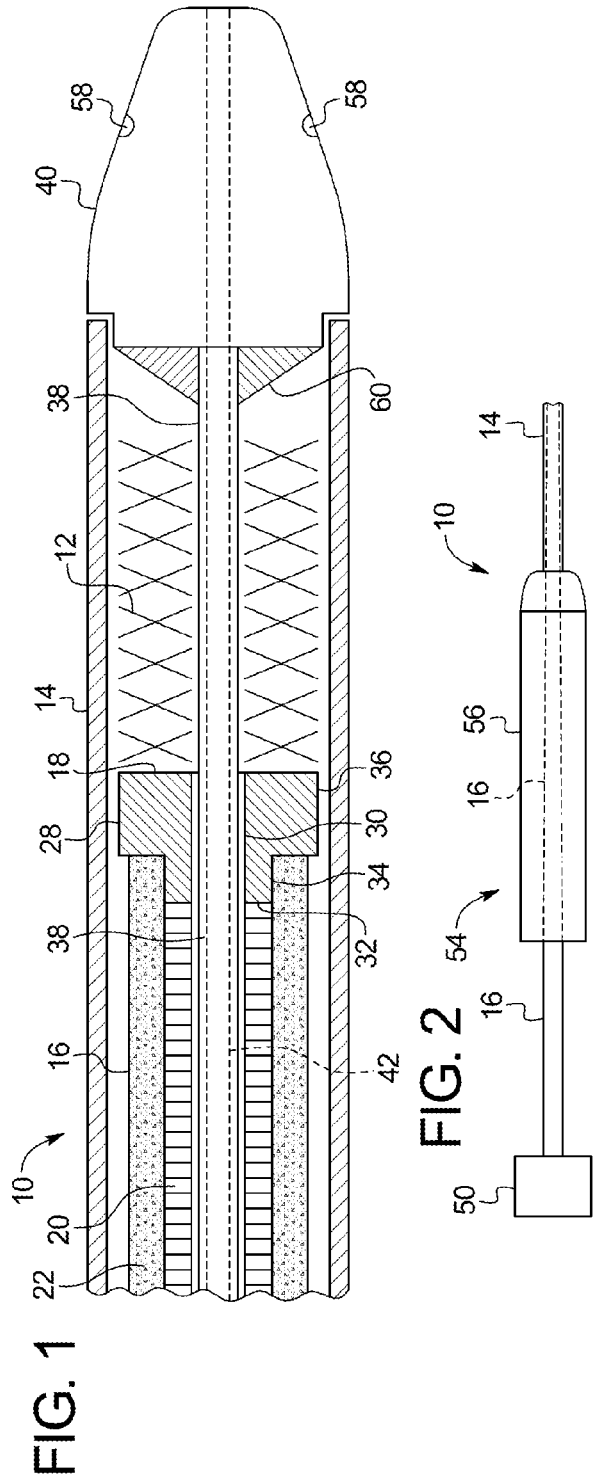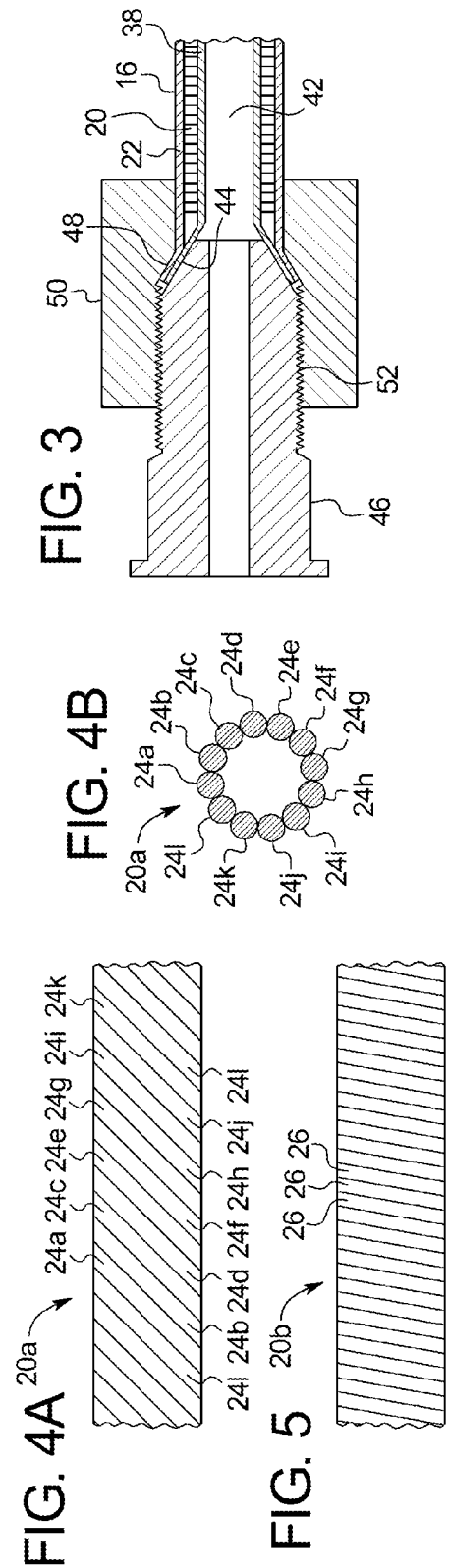

INNER CATHETER ARRANGEMENT FOR A SELF-EXPANDING MEDICAL DEVICE DELIVERY SYSTEM

This application claims priority to U.S. Provisional Application No. 61/765,252, filed Feb. 15, 2013, which is hereby incorporated by reference herein.

BACKGROUND

The present invention relates generally to medical devices and more particularly to delivery systems for medical devices.

Intraluminal medical devices are used by physicians to treat numerous conditions using minimally invasive procedures. Examples of intraluminal medical devices include stents, stent-grafts, filters, valves, etc. One type of intraluminal medical device that has become especially common is self-expanding stents. Typically, self-expanding medical devices, including stents, are made from an elastic structure that may be compressed into a low profile state that can be passed through vessels in a patient with minimal trauma. Once at the desired treatment site, the self-expanding medical device is released and self-expands like a spring until it contacts a tissue wall which prevents further expansion. Common materials that are used in self-expanding medical devices include nitinol and stainless steel, although other materials are also possible.

Self-expanding stents are used to treat various organs, such as the vascular system, colon, biliary tract, urinary tract, esophagus, trachea and the like. For example, stents are commonly used to treat blockages, occlusions, narrowing ailments and other similar problems that restrict flow through a passageway. One area where stents are commonly used for treatment involves implanting an endovascular stent into the vascular system in order to improve or maintain blood flow through narrowed arteries. However, stents are also used in other treatments as well, such as the treatment of aneurysms. Stents have been shown to be useful in treating various vessels throughout the vascular system, including both coronary vessels and peripheral vessels (e.g., carotid, brachial, renal, iliac and femoral). In addition, stents have been used in other body vessels as well, such as the digestive tract.

One type of delivery system for intraluminal medical devices includes an inner catheter and an outer sheath attached to a handle arrangement. One portion of the handle is typically connected to the inner catheter and another portion of the handle is typically connected to the outer sheath. The inner catheter extends coaxially through the outer sheath, and the two portions of the handle are arranged to longitudinally pull the outer sheath relative to the inner catheter. Thus, when the distal end of the delivery system is positioned within the patient's body at the intended treatment site, the physician actuates the handle outside the patient's body by moving the two portions relative to each other so that the outer sheath is withdrawn over the medical device and inner catheter. In the case of self-expanding medical devices, like stents, the outer sheath also serves to radially restrain the device in the compressed state until the outer sheath is withdrawn. As the outer sheath is withdrawn, the medical device is released in the body at the treatment site, and in the case of a self-expanding stent, the stent expands outward away from the inner catheter and presses against the vessel wall. Although the outer sheath is usually withdrawn by pulling the outer sheath proximally relative to the inner catheter, it may also be possible to withdraw the outer sheath by pushing the inner catheter distally relative to the outer sheath. After the medical device has been fully released from the delivery system, the handle may then be pulled by the physician to withdraw the inner catheter and outer sheath from the patient's body, while leaving the medical device implanted in the body.

Precise placement of intraluminal medical devices is a concern in most medical procedures. One problem that can contribute to imprecise placement of intraluminal medical devices is deflection of the delivery system during deployment. This can be a particular problem in the deployment of self-expanding medical devices, like stents, because the medical device presses outward against the inner surface of the outer sheath prior to deployment. When the outer sheath is withdrawn, the outward pressure exerted by the medical device creates friction between the medical device and the outer sheath. Since the medical device is typically prevented from moving proximally with the outer sheath by a stop attached to the inner catheter, the frictional force between the medical device and the outer sheath causes the outer sheath to be in tension and the inner catheter to be in compression. This can cause the inner catheter to contract in length due to the compressive force. In addition, the inner catheter can buckle, or snake, within the outer sheath. Both of these responses can cause the distal end of the inner catheter, and thus the medical device itself, to move proximally from the intended treatment site. Although the contraction and buckling may decrease somewhat as the outer sheath begins to withdraw from the medical device due to the release of some of the frictional force, the distal end of the inner catheter may not completely return to the intended treatment site when the medical device is initially released and implants within the patient's body. Moreover, the stent and/or inner catheter can build up sufficient spring force due to the contraction of the inner catheter and the stent to cause the stent to jump distally once the static friction is released. With medical devices that cause high frictional loads against the outer sheath, like drug coated stents, covered stents and particularly long stents, the initial deflection of the delivery system and subsequent distal movement due to the release of friction can make it difficult for a physician to predict the exact location where the medical device will be released in a patient's body.

Accordingly, the inventor believes it would be desirable to provide an improved delivery system for intraluminal medical devices.

SUMMARY

An improved delivery system is described. The delivery system has an outer sheath, a first inner catheter and second inner catheter. The outer sheath radially restrains a compressed medical device in the distal end of the outer sheath. The first inner catheter is disposed within the outer sheath and has a stop surface adapted to abut the proximal end of the medical device. The second inner catheter is disposed through the first inner catheter and extends distally past the stop surface. The first and second inner catheters are unattached to each other along at least a length of the delivery system that is intended to be inserted into a patient's body. The inventions herein may also include any other aspect described below in the written description, the claims, or in the attached drawings and any combination thereof.

BRIEF DESCRIPTION OF SEVERAL VIEWS OF THE DRAWINGS

The invention may be more fully understood by reading the following description in conjunction with the drawings, in which:

FIG. 1 is a partial cross-sectional view of a distal end of a delivery system;

FIG. 2 is a side view of a proximal end of the delivery system;

FIG. 3 is a cross-sectional view of a proximal end of a first and second inner catheter;

FIG. 4A is a side view of a multiple wire closed coil;

FIG. 4B is a cross-sectional end view of the multiple wire closed coil; and

FIG. 5 is a side view of a single wire closed coil.

DETAILED DESCRIPTION

Referring now to the figures, and particularly to FIGS. 1-2, a delivery system 10 for a medical device 12 is shown. As shown in FIG. 1, a medical device 12, such as a self-expanding stent 12, may be loaded into the distal end of the delivery system 10 within an outer sheath 14. As in a conventional delivery system, the stent 12 remains in a compressed state while disposed in the outer sheath 14 and exerts an outward force against the outer sheath 14. However, the outer sheath 14 restrains the medical device 12 to prevent it from expanding to its unrestrained expanded state.

As further shown in FIG. 1, the delivery system 10 is provided with a first inner catheter 16 disposed within the outer sheath 14. The first inner catheter 16 is designed to longitudinally restrain the stent 12 during deployment as the outer sheath 14 is withdrawn. Thus, the first inner catheter 16 prevents the stent 12 from moving proximally with the outer sheath 14 during deployment. Therefore, the first inner catheter 16 is provided with a stop surface 18 that abuts the proximal end of the stent 12 when the outer sheath 14 is withdrawn.

The body of the first inner catheter 16 is preferably a composite structure with a closed coil wire 20 and a polymer outer layer 22. The closed coil wire 20 is preferably made from one or more metal wires wound in a helical pattern to form a tube. For example, one embodiment of the closed coil wire 20 is shown in FIGS. 4A-4B, in which the closed coil wire 20a is made up of twelve wires 24a-l positioned side-by-side and wound around helically to form a tube. The wound wire tube 20 is a closed coil 20 in the sense that each wire winding substantially abuts against adjacent wire windings without substantial gaps between the windings. In FIGS. 4A-4B, because the closed coil wire 20a is formed of multiple wires 24a-l, each individual wire 24a-l abuts against a different wire 24a-l instead of abutting against itself. As a result, the individual wires 24a-l have a longer pitch than a single wire 26 closed coil 20b as shown in FIG. 5. As shown in FIG. 5, a closed coil wire 20b with a single wire 26 may also be used. However, because the wound wire to 20b is made of a single wire 26, the wire 26 substantially abuts against itself in each winding.

The outer layer 22 is adhered to the outer diameter of the closed coil wire 20. This is preferably accomplished by sliding the closed coil wire 20 into a thermoplastic tube 22, such as nylon. The thermoplastic tube 22 and closed coil wire 20 may then be disposed within a heat shrink tube. The heat shrink tube and thermoplastic tube 22 may then be heated to melt the thermoplastic tube 22 and contract the heat shrink tube. As a result, the thermoplastic tube 22 is squeezed against the closed coil wire 20 by the heat shrink tube and melts at least partially into the crevices between adjacent wire windings. Once the thermoplastic tube 22 cools, the heat shrink tube may be trimmed away from the thermoplastic tube 22. Thus, after forming, the thermoplastic tube 22 forms the outer layer 22 of the first inner catheter 16 and is melt bonded to the closed coil wire 20. Alternatively, the outer layer 22 could be extruded onto the closed coil wire 20 if desired.

The first inner catheter 16 is preferably provided with a metal ring 28 that forms the stop surface 18. The inner lumen 30 of the ring 28 may have a diameter that is substantially equal to the inner diameter of the closed coil wire 20. The ring 28 may also have a proximal portion 32 that has a reduced outer diameter 34 compared to the distal portion 36 that forms the stop surface 18. The ring 28 is preferably attached to the distal end of the first inner catheter 16 by extending the outer layer 22 of the first inner catheter 16 over the proximal portion 32 of the ring 28. The outer layer 22 is thus preferably adhered to the reduced outer diameter 34. The proximal end of the proximal portion 32 of the ring 28 also preferably abuts the end of the closed coil wire 20 so that deployment forces exerted on the ring 28 by the stent 12 are directly transmitted to the closed coil wire 20.

The second inner catheter 38 is disposed within the closed coil wire 20 and extends past the stop surface 18 and through the stent 12. At the distal end, the second inner catheter 38 may be attached to an atraumatic tip 40 that extends at least partially distal from the distal end of the outer sheath 14. The second inner catheter 38 also preferably includes a lumen 42 extending therethrough for a guidewire. The second inner catheter 38 may be made from various materials, such as polyether ether ketone (PEEK), polyimide or polytetrafluoroethylene (PTFE). For example, in a preferred embodiment, the second inner catheter 38 may have an outer structural layer, such as PEEK or polyimide, and an inner lubricious layer, such as PTFE. Thus, in this embodiment, the inner lubricious layer reduces friction between the guidewire and the guidewire lumen 42.

Although the second inner catheter 38 extends through the closed coil wire 20, the second inner catheter 38 is not attached to the first inner catheter 16 at least along a majority of the length between the deployment handle 54 and the distal end of the delivery system 10. For example, the first and second inner catheters may be attached at the stop ring 28 or at intermediate positions between the deployment handle 54 and the stop ring 28 with an adhesive or other bonding. More preferably, the first and second inner catheters 16, 38 are not attached to each other along the distal portion of the delivery system 10 that is adapted to be passed through a patient's body during a procedure up to the stop ring 28 (i.e., the second inner catheter 38 could be attached to the stop ring 28). However, it is more preferable for the second inner catheter 38 to not be attached to the first inner catheter 16 at the stop ring 28. Most preferably, the second inner catheter 38 is not attached to the first inner catheter 16 along the entire portion of the delivery system distal from the deployment handle 54. Although FIG. 1 depicts a small radial space between the first and second inner catheters 16, 38, this space is shown merely for illustration purposes to demonstrate that the first and second inner catheters 16, 38 are not attached to each other. However, it is preferable for the outer surface of the second inner catheter 38 and the inner surface of the first inner catheter 16 to be substantially in complete contact with each other with substantially no annular gap between the second inner catheter 38 and the first inner catheter 16. Thus, even though the first and second inner catheters 16, 38 are not attached to each other, the second inner catheter 38 may provide some support to the first inner catheter 16.

As shown in FIG. 3, the first and second inner catheters 16, 38 may be attached to each other at the proximal ends of the first and second inner catheters 16, 38. For example, the proximal ends of the first and second inner catheters 16, 38 may be flared and may be clamped between the taper 44 of a Luer fitting 46 and the reverse taper 48 of the housing 50. The flared ends may be clamped between the tapers 44, 48 of the fitting 46 and housing 50 by tightening a threaded connection 52 between the fitting 46 and the housing 50. As shown, the closed coil wire 20 need not be flared and clamped with the first and second inner catheters 16, 38. Numerous other ways of attaching the first and second inner catheters 16, 38 together along the proximal portion of the delivery system 10 that remains outside the patient's body are also possible.

As shown in FIG. 2, the deployment handle 54 may have a first handle member 50 and a second handle member 56. The first handle member 50 is attached to at least the first inner catheter 16, but as described above, the first handle member 50 may be attached to both the first inner catheter 16 and the second inner catheter 38. The second handle member 56 is attached to the outer sheath 14. Although other deployment handle arrangements are possible, in the described embodiment, the first and second inner catheters 16, 38 extend from the first handle member 50 and through the second handle member 56. In this design, it may also be desirable to provide a metal cannula around the first inner catheter 16 between the first handle member 50 and the second handle member 56. This may be useful to stiffen the portion of the first and second inner catheters 16, 38 that extends between the first and second handles 50, 56. A metal cannula around the first inner catheter 16 may also allow the second handle member 56 to slide smoothly toward the first handle member 50 along the metal cannula. For example, in FIG. 3, a metal cannula could be added as an additional layer around the first inner catheter 16 and could have a proximal flared end that is fixed between the tapers 44, 48 of the Luer fitting 46 and the first handle member 50 like the flared first and second inner catheters 16, 38.

In order to deploy the self-expanding stent 12 within a patient's body, the distal portion of the outer sheath 14 and first and second inner catheters 16, 38 (shown at least partially in FIG. 1) will be positioned within the patient's body. However, the proximal portion of the outer sheath 14 and first and second inner catheters 16, 38 and the deployment handle 54 (shown at least partially in FIG. 2) will remain outside the patient's body. Once the stent 12 is located at the desired treatment site within the patient's body, the physician will typically longitudinally restrain the first handle member 50. The physician may then pull the second handle member 56 proximally toward the first handle member 50. This causes the outer sheath 14 to move proximally relative to the first and second inner catheters 16, 38. However, because the proximal end of the stent 12 abuts the stop surface 18, the stent 12 is prevented from moving proximally with the outer sheath 14. Although a certain amount of friction will occur between the outer surface of the stent 12 and the inner surface of the outer sheath 14, the outer sheath 14 is forced to slide proximally relative to the stent 12. As a result, as the distal end of the outer sheath 14 slides past the stent 12, the stent 12 will self-expand outward toward the patient's vessel wall since the stent 12 is no longer radially restrained by the outer sheath 14. Although the first handle 50 is shown in FIG. 2 as a smaller knob 50 and the second handle 56 is shown as a larger housing 56, the design of the first and second handles 50, 56 could be reversed so that the first handle 50 is a larger housing and the second handle 56 is a knob that slides relative to the first handle 50. Various other types of deployment handles that provide relative longitudinal movement between the outer sheath 14 and the first inner catheter 16 are also possible.

One advantage of providing first and second inner catheters 16, 38 that are unattached to each other is that potential buckling of the closed coil wire 20 may be less likely to interfere with the guidewire lumen 40. Unlike conventional reinforcement structures used in various types of catheters, the closed coil wire 20 does not have any substantial longitudinal gaps between adjacent windings as explained above. This is desirable in the delivery system 10 described herein so that the compression force experienced by the first inner catheter 16 is transmitted directly through abutting windings without providing longitudinal gaps that might compress in length. However, one problem with closed coil wires 20 like this is that adjacent windings may slide over or under each other when compressive force is applied to the closed coil wire 20. That is, the coil tube 20 may have a tendency to buckle since adjacent wires directly contact each other. While the outer polymer layer 22 that is adhered to the closed coil wire 20 may discourage buckling of the closed coiled wire 20, there is still the possibility that the closed coil wire 20 may at least partially buckle if a large compressive force is applied to the first inner catheter 16. If the second inner catheter 38 was attached to the closed coil wire 20 along its length in a more conventional design, the second inner catheter 38 would also buckle in direct response to the closed coil wire 20. However, this could result in a substantial deformation of the guidewire lumen 40 which could cause interference with the guidewire. This problem is improved in the described embodiment because the second inner catheter 38 is not directly attached to the closed coil wire 20 along its length. Thus, at least a small amount of movement is possible between the closed coil wire 20 and the second inner catheter 38 to accommodate moderate buckling of the closed coil wire 20. As a result, even if the closed coil wire 20 buckles slightly or moderately, the second inner catheter 38 may smoothly deflect around the buckled portion without substantially deforming the guidewire lumen 40.

The design of the first and second inner catheters 16, 38 also makes it possible to improve the positioning of the first and second catheters 16, 38 relative to the stent 12 in the outer sheath 14. Conventionally, the portion of the inner catheter extending through the stent 12 and connected to the distal tip 40 is integral with or otherwise attached to the body of the inner catheter. In this design, the stent 12 is typically loaded into the outer sheath 14, and the inner catheter is positioned in the outer sheath 14 so that the stop surface 18 is adjacent the proximal end of the stent 12. The distal tip 40 is then bonded onto the end of the inner catheter. However, the problem with this design is that extra longitudinal space is required to allow the tip 40 to be bonded onto the inner catheter. The additional space is typically required to permit the tip 40 to be glued on while ensuring that the glue does not contact the stent 12.

In the described embodiments, the delivery system 10 may be assembled by first compressing and loading the stent 12 into the distal end of the outer sheath 14 so that the outer sheath 14 radially restrains the stent 12. Preferably before the first and second inner catheters 16, 38 are inserted into the outer sheath 14, a pusher ring 28 is bonded to the distal end of the first inner catheter 16, and an atraumatic tip 40 is bonded onto the distal end of the second inner catheter 38. The first inner catheter 16 is then slid through the proximal end of the outer sheath 14, and the second inner catheter 38 is slid through the distal end of the outer sheath 14. Regardless of which order the first and second inner catheters 16, 38 are inserted, the second inner catheter 38 will slide through the inner lumen 30 of the first inner catheter 16 and pusher ring 28. The pusher ring 28 is then positioned in the outer sheath 14 adjacent the proximal end of the stent 12 so that the pusher ring 28 can abut the end of the stent 12. Likewise, the tip 40 is positioned adjacent the distal end of the stent 12. Unlike conventional manufacturing methods, the glue injected into the glue ports 58 and the glue 60 along the proximal end of the tip 40 will be cured at this stage so there is no concern about the glue 60 contacting the stent 12. As a result, the tip 40 and the pusher ring 28 may be positioned immediately adjacent the distal and proximal ends of the stent 12, respectively. The proximal ends of the first and second inner catheters 16, 38 may then be fixed together to set the longitudinal space between the tip 40 and the pusher ring 28, while leaving the remaining length of the first and second inner catheters 16, 38 unattached. This may be done as shown in FIG. 3 or in any other desirable way.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A self-expanding medical device delivery system, comprising:
    an outer sheath extending along a proximal portion and a distal portion, said proximal portion being adapted to be attached to a deployment handle and remain outside of a patient's body, said distal portion being adapted to be positioned within said patient's body;
    a self-expanding medical device disposed within said distal portion of said outer sheath, said self-expanding medical device being in a compressed state and exerting an outward force against said outer sheath, wherein said outer sheath restrains said medical device from expanding;
    a first inner catheter disposed within said outer sheath and extending from adjacent a proximal end of said medical device to said deployment handle, said first inner catheter comprising a closed coil wire and a polymer outer layer adhered to an outer diameter of said closed coil wire, said first inner catheter comprising a stop surface adapted to abut said proximal end of said medical device, a ring attached to a distal end of said first inner catheter, said ring defining said stop surface and comprising an inner lumen extending therethrough with a diameter substantially equal to an inner diameter of said closed coil wire, said ring comprising a proximal portion with a reduced outer diameter, wherein a proximal end of said proximal portion abuts said closed coil wire and said outer layer is disposed over said proximal portion and is adhered to said reduced outer diameter; and
    a second inner catheter disposed within said closed coil wire and extending from past said stop surface and through said medical device to said deployment handle, said second inner catheter being unattached to said first inner catheter along a majority of a length between said deployment handle and said stop surface.

2. The self-expanding medical device delivery system according to claim 1, wherein said medical device is a stent.

3. The self-expanding medical device delivery system according to claim 1, wherein said second inner catheter comprises a guidewire lumen extending therethrough.

4. The self-expanding medical device delivery system according to claim 1, further comprising an atraumatic tip attached to a distal end of said second inner catheter, said tip extending at least partially distal from a distal end of said outer sheath.

5. The self-expanding medical device delivery system according to claim 1, wherein said closed coil wire comprises a single wound metal wire.

6. The self-expanding medical device delivery system according to claim 1, wherein said closed coil wire comprises multiple wound metal wires.

7. The self-expanding medical device delivery system according to claim 1, wherein said outer layer is a thermoplastic polymer and said closed coil wire is a metal, said thermoplastic polymer being melt bonded to said metal to adhere said outer layer to said closed coil wire.

8. The self-expanding medical device delivery system according to claim 7, wherein said first inner catheter and said second inner catheter are fixed together at said deployment handle.

9. The self-expanding medical device delivery system according to claim 8, wherein there is substantially complete contact between an outer surface of said second inner catheter and an inner surface of said first inner catheter, there being substantially no annular gap between said second inner catheter and said first inner catheter, and said second inner catheter is unattached to said first inner catheter along an entire length distal from said deployment handle.

10. The self-expanding medical device delivery system according to claim 1, wherein said first inner catheter and said second inner catheter are fixed together at said deployment handle.

11. The self-expanding medical device delivery system according to claim 1, wherein there is substantially complete contact between an outer surface of said second inner catheter and an inner surface of said first inner catheter, there being substantially no annular gap between said second inner catheter and said first inner catheter.

12. The self-expanding medical device delivery system according to claim 1, wherein the ring is a metal ring.

13. The self-expanding medical device delivery system according to claim 1, wherein said second inner catheter is unattached to said first inner catheter along an entire length distal from said deployment handle.

14. The self-expanding medical device delivery system according to claim 13, wherein said medical device is a stent, said second inner catheter comprises a guidewire lumen extending therethrough, and further comprising an atraumatic tip attached to a distal end of said second inner catheter, said tip extending at least partially distal from a distal end of said outer sheath.

15. The self-expanding medical device delivery system according to claim 14, wherein said outer layer is a thermoplastic polymer and said closed coil wire is a metal, said thermoplastic polymer being melt bonded to said metal to adhere said outer layer to said closed coil wire, and said first inner catheter and said second inner catheter are fixed together at said deployment handle.

16. The self-expanding medical device delivery system according to claim 1, wherein there is substantially complete contact between an outer surface of said second inner catheter and an inner surface of said first inner catheter, there being substantially no annular gap between said second inner catheter and said first inner catheter.

17. The self-expanding medical device delivery system according to claim 16, wherein said closed coil wire comprises a single wound metal wire.

18. The self-expanding medical device delivery system according to claim 16, wherein said closed coil wire comprises multiple wound metal wires.

* * * * *